United States Patent [19]

Van Gestel

[11] Patent Number: 5,712,275
[45] Date of Patent: Jan. 27, 1998

[54] ANTIBACTERIAL AND ANTIFOULING OXATHIAZINES AND THEIR OXIDES

[75] Inventor: Jozef Frans Elizabetha Van Gestel, Vosselaar, Belgium

[73] Assignee: Janssen Pharmaceutica, N.V., Beerse, Belgium

[21] Appl. No.: 586,690

[22] PCT Filed: Aug. 24, 1994

[86] PCT No.: PCT/EP94/02784

§ 371 Date: Jan. 25, 1996

§ 102(e) Date: Jan. 25, 1996

[87] PCT Pub. No.: WO95/05739

PCT Pub. Date: Mar. 2, 1995

Related U.S. Application Data

[63] Continuation-in-part of Ser. No. 111,352, Aug. 24, 1993, abandoned.

[51] Int. Cl.[6] .................. A61K 31/54; A01N 43/34; A01N 43/36; A01N 43/72
[52] U.S. Cl. .................. 514/222.5; 504/155; 504/156; 504/221
[58] Field of Search .................. 504/155, 156, 504/221; 514/222.5

[56] References Cited

U.S. PATENT DOCUMENTS 4,569,690  2/1986  Brouwer et al. .................. 71/90

FOREIGN PATENT DOCUMENTS 0 104 940  4/1984  European Pat. Off. .................. 291/6

*Primary Examiner*—Allen J. Robinson
*Attorney, Agent, or Firm*—Charles J. Metz

[57] ABSTRACT

Use of 3-aryl-5,6-dihydro-1,4,2-oxathiazines and their oxides having the formula

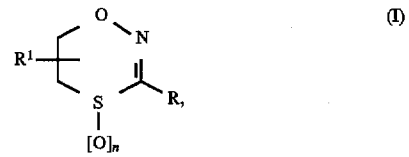

wherein n is 0, 1 or 2; $R^1$ is hydrogen, $C_{1-4}$alkyl or benzyl; and R represents (a) phenyl; phenyl substituted with 1 to 3 substituents independently selected from hydroxyl, halo, $C_{1-12}$alkyl, $C_{5-6}$cycloalkyl, trihalomethyl, phenyl, $C_{1-5}$alkoxy, $C_{1-5}$alkylthio, tetrahydropyranyloxy, phenoxy, $C_{1-4}$alkylcarbonyl, phenylcarbonyl, $C_{1-4}$alkylsulfinyl, $C_{1-4}$alkylsulfonyl, carboxy or its alkali metal salt, $C_{1-4}$alkyloxycarbonyl, $C_{1-4}$alkylaminocarbonyl, phenylaminocarbonyl, tolylaminocarbonyl, morpholinocarbonyl, amino, nitro, cyano, dioxolanyl or $C_{1-4}$alkyloxyiminomethyl; naphthyl; pyridinyl; thienyl, preferably when n is not 2; furanyl; or thienyl or furanyl substituted with one to three substituents independently selected from $C_{1-4}$alkyl, $C_{1-4}$alkyloxy, $C_{1-4}$alkylthio, halo, cyano, formyl, acetyl, benzoyl, nitro, $C_{1-4}$alkyloxycarbonyl, phenyl, phenylaminocarbonyl and $C_{1-4}$alkyloxyiminomethyl; or R represents a radical of formula

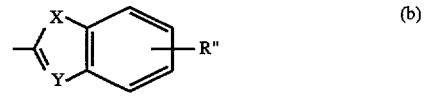

wherein X is oxygen or sulfur; Y is nitrogen, CH or $C(C_{1-4}$alkyloxy); and R" is hydrogen or $C_{1-4}$alkyl, as an antibacterial, anti-yeast, antifungal, algicidal, anti-crustacean, molluscicidal and general antifouling agent and compositions containing the same.

11 Claims, No Drawings

ANTIBACTERIAL AND ANTIFOULING OXATHIAZINES AND THEIR OXIDES

CROSS-REFERENCE TO RELATED APPLICATIONS

This application is a 371 of PCT application Ser. No. PCT/EP 94/02784, filed Aug. 24, 1994, which is a C-I-P of U.S. patent application Ser. No. 08/111,352, filed on Aug. 24, 1993, now abandoned.

The present invention concerns a method of controlling bacteria and fouling organisms with 3-aryl-5,6-dihydro-1,4,2-oxathiazines and their oxides, a method of protecting non-living materials other than wood, and industrial antibacterial and antifouling compositions. Surfaces of objects exposed to humid or aqueous environments are readily colonized by micro-organisms and occasionally by other, higher life forms such as molluscs and crustacea. As these organisms settle on or attach to said surfaces, the value of the exposed objects diminishes. The exterior, but possibly also the interior of the object may deteriorate, the surface changes (e.g. from smooth, clean and streamlined to rough, foul and turbulent), the weight of the object increases by the deposit of the organisms and their remnants, and the vicinity of the object may become obstructed or encumbered. The function of the object and system involved lowers and the quality of the aqueous environment deteriorates. Similar problems beset industrially used compositions such as coatings, lubricants and the like. All these phenomena are referred to as fouling. The oxathiazines of the present method and their oxides are disclosed in U.S. Pat. No. 4,569,690 as herbicides, plant fungicides, plant desiccants and defoliants.

The present invention provides a method of controlling bacteria and fouling organisms, said method comprising applying to said bacteria or fouling organisms, or to the locus thereof an effective antibacterial or antifouling amount of a compound having the formula

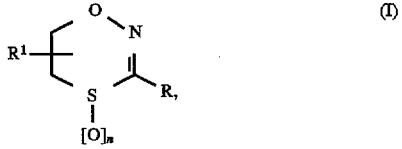

wherein n is 0, 1 or 2; $R^1$ is hydrogen, $C_{1-4}$alkyl or benzyl; and R represents (a) phenyl; phenyl substituted with 1 to 3 substituents independently selected from hydroxyl, halo, $C_{1-12}$alkyl, $C_{5-6}$cycloalkyl, trihalomethyl, phenyl, $C_{1-5}$alkoxy, $C_{1-5}$alkylthio, tetrahydropyranyloxy, phenoxy, $C_{1-4}$alkylcarbonyl, phenylcarbonyl, $C_{1-4}$alkylsulfinyl, $C_{1-4}$alkylsulfonyl, carboxy or its alkali metal salt, $C_{1-4}$alkyloxycarbonyl, $C_{1-4}$alkylaminocarbonyl, phenylaminocarbonyl, tolylaminocarbonyl, morpholinocarbonyl, amino, nitro, cyano, dioxolanyl or $C_{1-4}$alkyloxyiminomethyl; naphthyl; pyridinyl; thienyl, preferably when n is not 2; furanyl; or thienyl or furanyl substituted with one to three substituents independently selected from $C_{1-4}$alkyl, $C_{1-4}$alkyloxy, $C_{1-4}$alkylthio, halo, cyano, formyl, acetyl, benzoyl, nitro, $C_{1-4}$alkyloxycarbonyl, phenyl, phenylaminocarbonyl and $C_{1-4}$alkyloxyiminomethyl; or R represents a radical of formula

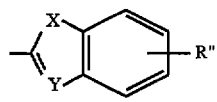

wherein X is oxygen or sulfur; Y is nitrogen, CH or $C(C_{1-4}$alkyloxy); and R" is hydrogen or $C_{1-4}$alkyl.

The present invention in particular provides a method of protecting non-living materials other than wood, and the objects made of or covered by said non-living materials, against bacteria and/or fouling organisms, said method comprising applying to the surface or incorporating into said materials or objects an effective antibacterial or antifouling amount of a compound of formula (I).

In the foregoing definitions halo is generic to fluoro, chloro, bromo and iodo; $C_{1-4}$alkyl defines straight and branch chained saturated hydrocarbon radicals having from 1 to 4 carbon atoms comprising methyl, ethyl, n-propyl, 1-methylethyl, n-butyl, 1,1-dimethylethyl, 1-methylpropyl, 2-methylpropyl; $C_{1-5}$alkyl includes $C_{1-4}$alkyl radicals as defined above and saturated hydrocarbon radicals having five carbon atoms, e.g. n-pentyl and the branched pentyl isomers; $C_{1-6}$alkyl includes $C_{1-5}$alkyl radicals as defined above and six carbon containing homologs, e.g. n-hexyl and the branched hexyl isomers. $C_{1-12}$alkyl includes $C_{1-6}$alkyl and saturated hydrocarbon radicals having from 7 to 12 carbon atoms, e.g. heptyl, octyl, nonyl, decyl, undecyl and their isomers. The term alkali metal cation in particular is a sodium or potassium cation. Trihalomethyl defines a methyl group being fully substituted with halo atoms, in particular trifluoromethyl and trichloromethyl. $C_{1-4}$alkyloxyiminomethyl defines a radical of formula —CH=N—O—$C_{1-4}$alkyl.

Particular compounds of formula (I) for use in the method are those wherein n is 0, 1 or 2; $R^1$ is hydrogen, $C_{1-4}$alkyl or benzyl; and R represents phenyl; naphthyl; pyridinyl; thienyl provided that n is not 2; furanyl optionally substituted with 1 to 3 substituents independently selected from $C_{1-4}$alkyl and $C_{2-5}$alkyloxycarbonyl; or phenyl substituted with 1 or 2 substituents indepently selected from hydroxyl, halo, $C_{1-12}$alkyl, $C_{5-6}$cycloalkyl, trihalomethyl, phenyl, $C_{1-5}$alkoxy, $C_{1-5}$alkylthio, tetrahydropyranyloxy, phenoxy, $C_{2-5}$alkylcarbonyl, phenylcarbonyl, $C_{1-4}$alkylsulfinyl, $C_{1-4}$alkylsulfonyl, carboxy or its alkali metal salt, $C_{1-5}$alkoxycarbonyl, $C_{2-5}$alkylaminocarbonyl, phenylaminocarbonyl, tolylaminocarbonyl, morpholinocarbonyl, amino, nitro, cyano, or dioxolanyl.

Of interest are those compounds wherein n is 1 and R represents phenyl, thienyl or phenyl substituted with one or two substituents selected from halo and trihalomethyl; or those wherein n is 2 and R represents phenyl or phenyl substituted with one or two substituents selected from halo and trihalomethyl.

Of further interest are the compounds wherein $R^1$ is hydrogen, n is 1 or 2, and R represents phenyl, $C_{1-6}$alkylphenyl, halophenyl, dihalophenyl, biphenyl, $C_{1-5}$alkyloxyphenyl, trihalomethylphenyl, nitrophenyl, phenyl substituted with $C_{2-5}$alkyloxycarbonyl, $C_{1-6}$alkylnitrophenyl, unsubstituted furanyl or thienyl, or furanyl or thienyl substituted with ethoxycarbonyl, cyano, chlorine or bromine.

Of particular interest are the compounds wherein $R^1$ is hydrogen, n is 1 or 2, and R represents 3-fluorophenyl, 4-chlorophenyl, 3,4-dichlorophenyl, 3,5-dichlorophenyl, 3-trifluoromethylphenyl, 4-trifluoromethylphenyl, 4-methylphenyl, 3-ethanonephenyl, 3-nitrophenyl, 3-methyl-4-nitrophenyl or 2-thienyl.

Also of further interest are those compounds of formula (I) wherein $R^1$ is hydrogen, R is a radical of formula (b) wherein X is sulfur, Y is nitrogen or CH, and R" is hydrogen.

Preferred compounds are 5,6-dihydro-3-(2-thienyl)-1,4,2-oxathiazine, 4-oxide and 3-(4-chlorophenyl)-5,6-dihydro-1,4,2-oxathiazine, 4,4-dioxide.

All compounds of formula (I) can be prepared following the procedures described in U.S. Pat. No. 4,569,690.

The compounds of formula (I) are active against gram-positive bacteria and, more importantly for use in material protection, also against gram-negative bacteria. Susceptible bacteria belong to genera such as Aeromonas, Alcaligenes, Brevibacterium, Cellulomonas, Citrobacter, Corynebacterium, Enterobacter, Escherichia, Klebsiella, Micrococcus, Proteus, Providencia, Pseudomonas, Shewanella, Acinobacter, Bacillus, Serratia, Staphylococcus, Streptococcus and Xanthomonas.

The compounds of formula (I) further are active against fouling organisms. The term "fouling organisms" is meant to comprise organisms that grow on or adhere to various kinds of surfaces, in particular in humid or aqueous environments such as, marine waters, fresh waters, brackish waters, rain water, and also cooling water, drainage water, waste water and sewage. Fouling organisms are Algae such as, for example, Microalgae, e.g. Amphora, Achnanthes, Navicula, Amphipora, Melosira, Cocconeis, Chlamydomonas, Chlorella, Ulothrix, Anabaene, Phaeodactylum, Porphyridium; Macroalgae, e.g. Enteromorpha, Cladophora, Ectocarpus, Acrochaetium, Ceramium, Polysiphonia; Molluscs, e.g. Mytilus, Crustacea, e.g. Artemia, Balanus, Elminius Modestus, Verruca, Lepas and Ascidia, Hydrozoa and Bryozoa.

The present invention also provides a method for the preservation of non-living materials other than wood against fungi that spoil or destroy such materials. Said method involves treating such materials with an effective fungicidal amount of a compound of formula (I).

The compounds of formula (I) are useful to protect a wide variety of non-living materials other than wood, and the objects made thereof or covered thereby. Examples of non-living materials and the objects made thereof or covered thereby comprise adhesives; sizes; paper and cardboard; pulp; textiles; leather; paints; plastics, e.g. PVC and polyester; industrial compositions such as cooling media, e.g. cooling lubricants and cutting fluids, coating compositions, bath compositions (process liquids), lubricants and the like; metals and alloys such as iron and steel; building materials, e.g. bricks, (paving) stones, cement and concrete; decorating materials, e.g. plaster, tiles; and any other materials that can be contaminated or destroyed by bacteria, fungi or fouling organisms.

Of particular interest are coating materials conventionally employed for decorative and protective purposes. The present method is especially suited for protecting adherent coatings, whether clear or colored (i.e. comprising one or more dyes or pigments), and whether natural or synthetic, such as, for example, paints—especially antifouling paint compositions—, varnishes, lacquers, finishes, whitewash and similar coatings. The particular aptness of the present method of protecting said coating materials resides in the fact that the oxathiazines employed in the method not only effectively protect the coating material in storage containers, during "in can" conservation (especially against bacteria) thus ensuring a long pot (or can) life and good storage stability, but also effectively protect the coating material and optionally its underlying substrate when it has been applied as a film to said substrate ("film" conservation). The simultaneous utility of the oxathiazines for both "in can" and "film" conservation of coatings is of great practical value.

As constructions made of or covered by said non-living materials there can be mentioned swimming pools, baths, cooling water circulation circuits and industrial baths in various installations, e.g. in manufacturing plants or in air-conditioning installations, the function of which can be impaired by the presence and/or the multiplication of bacteria and fouling organisms. Further examples are buildings and parts of buildings such as floors, outer and inner walls or ceilings, of places suffering from dampness such as cellars, bathrooms, kitchens, washing houses and the like, and which are hot-beds for bacteria and/or fouling organisms. The presence of these organisms not only is problematic from the viewpoint of hygiene and aesthetics, but also causes economic losses because said buildings and/or decorating materials deteriorate more rapidly than desired.

The method is especially suitable to protect underwater objects such as, for example, shiphulls, harbour installations, drying docks, sluice-gates, locks, mooring masts, buoys, drilling platforms, bridges, pipelines, fishing nets, cables and any other object in constant or frequent contact with water, by applying to said objects an antifouling composition, e.g. paint composition, comprising an effective antifouling amount of a compound of formula (I).

In this context it should be noted that the present method provides a safer and ecologically more acceptable alternative for current methods using antifouling products based on heavy metals such as cuprous oxide and the like, for those based on organometallic derivatives such as organo-tin compounds. The toxicity of the oxathiazines to mammals is acceptable and as such they are less hazardous for humans whether these compounds reach the human body by direct physical contact (e.g. during handling or application) or via the food chain. Their bio-degradability ensures that they are less persistent in the environment and that they cause less and shorter environmental pollution and stress. The chemical stability of the oxathiazines furthermore implies that they are compatible with most non-living materials as such and do need special precautions such as the addition of agents for stabilizing the active ingredient. In materials that should form films such as lubricants, cutting fluids and coating materials, they do not impair the formation of uniform films and the practicability. In particular, in coating materials they do not impair rapid curing in practical circumstances such as room temperature and outdoor conditions, and allow for strong adhesion of the composition to the substrate and/or the topcoat.

The method of application is chosen in accordance with the intended objective and the prevailing circumstances. For instance, the technique used in the case of protecting lubricants, coatings or cutting fluids comprises mixing the active ingredient in said lubricants, coatings or fluids either during the manufacturing process or alternatively afterwards in the finished product. The active ingredient can be added in neat form or dissolved or suspended in a sufficient amount of diluent. Preferably the diluent consists of one or more of the solvents as they occur in the final composition.

The method also comprises applying compounds of formula (I), optionally in an appropriate formulation, to non-living materials by any of the techniques known in the art such as, for example, brushing, spraying, atomising, dipping, soaking, immersing, scattering and pouring. In some instances, the application may involve impregnation techniques using pressure or vacuum systems, thermal systems, injection or diffusion.

Appropriate formulations are formulated following art-known procedures to emulsifiable concentrates, directly sprayable or dilutable solutions, dilute emulsions, wettable powders, soluble powders, pastes, dusts, granulates, coating compositions, e.g. paints—in particular antifouling paint compositions—, lacquers and the like. For example, the active compound can be mixed with an extender, which consists of a liquid, semi-solid or solid carrier, and optionally surface-active agents such as emulsifiers and/or dispersing agents. In coating compositions, the active compound may advantageously be incorporated in polymers, copolymers or resins. These can consist of such monomers as dialkyl (dimethyl) siloxanes, (meth)acrylic add, (meth) acrylic acid esters, vinyl and allyl alcohols and derived esters (e.g. vinyl acetate), maleic acid, styrene, vinylchloride, butadiene, acrylamide, acrylonitrile and the like copolymerizable monomers. As resins there may be mentioned alkyd resins, polyurethanes, epoxy resins, phenolic resins and urea-formaldehyde resins. Further useful additives in said compositions comprise water-repelling agents and surface slipping agents that are capable of imparting a low surface tension of the coating film formed by the polymer or copolymer in the coating compositions.

Any suitable carrier or additive that does not interfere with the antibacterial nor the antifouling activity of the active ingredient can be used in the compositions of the present invention. The solid carriers or fillers used e.g. for dusts and powders include various inert, porous and pulverous distributing agents of inorganic or organic nature such as, for example, the natural mineral fillers, e.g. calcite, talcum, kaolin, montmorillonite or attapulgite, or fillers of organic nature, e.g. powdered cork, sawdust and other fine pulverous materials. In order to improve their physical properties it can be advantageous to add highly dispersed silicic acid or highly dispersed absorbent polymers. Suitable granulated absorbent carriers are of the porous type, for example, pumice, broken brick, sepiolite or bentonite; and suitable nonsorbent carriers are materials such as calcite or sand. The active ingredient is mixed with these carrier substances, for example, by being ground therewith; alternatively, the inert carrier substance is impregnated with a solution of the active component in a readily volatile solvent and the solvent is thereafter removed by heating or by filtering with suction at reduced pressure. By adding wetting and/or dispersing agents, such pulverous preparations can also be made readily wettable with water, so that suspensions are obtained upon dilution.

Inert diluents used for the production of liquid preparations should preferably not be readily inflammable and should be as far as possible non-toxic to non-target animals or plants and humans in the relevant surrounding. Diluents suitable for this purpose are, for example, water or, organic solvents such as, for example, aromatic hydrocarbons, e.g. methylbenzene, dimethylbenzene mixtures, substituted naphthalenes; alcohols and glycols and their ethers and esters, e.g. ethanol, ethylene glycol, ethylene glycol monomethyl or monoethyl ether; ketones e.g. 2-propanone, cyclohexanone and the like; strongly polar solvents; e.g. N-methyl-2-pyrrolidone, dimethyl sulfoxide or dimethylformamide; vegetable oils or epoxidised vegetable oils such as epoxidised coconut oil or soybean oil, and mixtures thereof. Solutions can be prepared in the usual way, if necessary, with assistance of solution promotors. Other liquid forms which can be used consist of emulsions, dispersions or suspensions of the active compound in water or suitable inert diluents, or also concentrates for preparing such emulsions, dispersions or suspensions which can be directly adjusted to the required concentration. For this purpose, the active ingredient is, for example, mixed with a dispersing, suspending or emulsifying agent. The active component can also be dissolved or dispersed in a suitable inert solvent and mixed simultaneously or subsequently with a dispersing or emulsifying agent. It is also possible to use semi-solid carrier substances of cream, ointment, paste or waxlike nature, into which the active ingredient can be incorporated, if necessary, with the aid of solution promotors and/or emulsifiers. Vaseline, petroleum wax, liquid paraffin, silicone oil and other cream-bases are examples of semi-solid carrier substances. Furthermore, it is possible for the active ingredient to be used in the form of aerosols. For this purpose the active ingredient is dissolved or dispersed in a volatile liquid suitable for use as a propellant, for example, chlorinated and/or chlorinated derivatives of methane and ethane and mixtures thereof, or compressed air. In this way solutions under pressure are obtained which, when sprayed, yield aerosols that are particularly suitable for controlling or combatting bacteria and/or fouling organisms, e.g. in closed chambers and storage rooms. For the latter purpose also smoke generators containing the active ingredient can be used.

Besides the compounds of formula (I) and the carrier, appropriate formulations often comprise other adjuvants conventionally employed in the art of formulation. These depend on specific applications and the user's preference. Such adjuvants are, for example, organic binding agents (e.g. chemically drying organic binder-forming polymers such as alkyd resins or physically drying organic binderforming solids by solvent evaporation); insecticides such as, for example, chlorinated hydrocarbons, e.g. endosulfan, organophosphates, e.g. chloropyriphos, pyrethroids, e.g. permethrin and the like; additional fungicides and bactericides such as alcohols, e.g. ethanol, 2,3,3-tri-iodallyl alcohol; aldehydes, e.g. formaldehyde, glutaraldehyde; formaldehyde releasing compounds, e.g. 2-bromo-2-nitro-propane-1,3-diol (bronopol), 2-bromo-2-nitro-propan-1-ol; reaction products of amines and formaldehyde, e.g. triazines, 3,5-dimethyltetrahydro-1,3,5-2H-thiadiazine-2-thione; reaction products of amides and formaldehyde, e.g. 1-hydroxymethyl-2-thiono-1:2-dihydro-benzothiazol-N-hydroxymethylbenzothiazolinthione; phenols, e.g. 2-phenylphenol, pentachlorophenol; organic acids, e.g. propionic acid, benzoic acid, salicylic acid, naphthenic acid copper salts; inorganic acids, e.g. boric acid; amides, e.g. 2,5-dimethyl-N-cyclohexyl-N-methoxy-furan-3-carbonamide; carbamates, e.g. 3-iodopropargyl-N-butylcarbamate (IPBC), methyl-N-benzimidazol-2-ylcarbamate (Carbendazim), methyl-N-(1-butylcarbamoyl)benzimidazol-2-ylcarbamate (benomyl), zinc dimethyldithiocarbamate, zinc ethylenebisdithiocarbamate, bis-(dimethylthiocarbamoyl)disulphide; pyridine derivatives, e.g. 2-mercapto-pyridine-N-oxide, 2-chloro-6-(trichloromethyl)pyridine, 2,3,5,6-tetrachloro-4-(methylsulphonyl)pyridine, copper 8-hydroxyquinoline, 1-ethyl-1,4-dihydro-7-methyl-4-oxo-1,8-naphthyridine-3-carboxylic acid; azoles, e.g. tebuconazole, propiconazole, azaconazole, imazalil; heterocyclic compounds, e.g. 2-methyl-3(2H)-isothiazolone, 5-chloro-2-methyl-3(2H)-isothiazolone, 2-n-octyl-4-isothiazolin-3-one, 4,5-dichloro-2-(n-octyl)-4-isothiazolin-3-one, 1,2-benzisothiazolin-3-one, 2-methyl-4,5-trimethylene-4-isothiazolin-3-one, 2-(4-thiazolyl)-benzimidazole, 2-mercaptobenzothiazole, 2-(thiocyanomethylthio)benzthiazole; N-haloalkylthio compounds, e.g. N-trichloromethylthiophthalimide, folpet, N-trichloromethylthio-4-cyclohexane-1,2-dicarboximide, captan, N-1,1,2,2-tetrachloroethylthio-4-cyclohexene-1,2-dicarboximide, captafol, dichlofluanide, tolylfluanide; compounds with activated halogen groups, e.g. chlorothalonil; surface active agents, e.g. guanidines and biguanides; organometallic compounds, e.g. bis(tri-n-butyltin-oxide, tributyltin esters, tributyltin naphthenate, tributyltin linoleate, tributyltin benzoate, tributyltin fluoride; various compounds, e.g. pimaricine, tridemorph, methylene bisthiocyanate, tolyl sulfone, dicyanobutane; metal salts, e.g. chrome-copper-arsenic; active natural products, e.g. streptomycin; auxiliary solvents such as ethylglycol acetate and methoxypropylacetate; processing additives; fixatives such as carboxymethylcellulose, polyvinyl alcohol, paraffin; plasticizers such as benzoic acid esters and phthalates, e.g. dibutyl phthalate, dioctyl phthalate, didodecyl phthalate; UV-stabilizers or stability enhancers; dyes; color pigments; siccatives such as cobalt octoate, lead octoate and cobalt naphthenate; corrosion inhibitors; antisettling agents; anti-skinning agents such as methyl ethyl ketoxime; antifoaming agents and the like. Generally, the adjuvants are not essential to the practice of the present invention but are included in particular formulations, especially in coating formulations to optimize overall effectiveness and ease of application. They can be used therein in the conventional amounts.

The antibacterial and/or antifouling compositions which are employed in the method of the invention can contain from 0.001% to 95% of the active ingredient by weight based on the total weight of the composition. Ready-to-use compositions such as paints preferably contain from 0.5% to 20%, in particular from 1 to 10% by weight of the active ingredient. Antifouling paint compositions on the other hand can contain from 10 up to 75%, in particular from 20 to 70% of the active ingredient of formula (I) by weight based on the total weight of the dry mass of said composition (i.e. up to 50%, in particular from 5 to 25% of the active ingredient by weight based on the total weight of the antifouling composition). Preferred compositions are composed in particular of the following constituents (all percentages are by weight):

| Emulsifiable concentrates | | |
|---|---|---|
| active ingredient: | 1 to 20%, preferably | 5 to 10% |
| surfactant: | 5 to 30%, preferably | 10 to 20% |
| liquid carrier: | 50 to 94%, preferably | 70 to 85% |
| Dusts | | |
| active ingredient: | 0.1 to 10%, preferably | 0.1 to 1% |
| solid carrier: | 99.9 to 90%, preferably | 99.9 to 99% |
| Suspension concentrates | | |
| active ingredient: | 5 to 75%, preferably | 10 to 50% |
| water: | 94 to 25%, preferably | 88 to 30% |
| surfactant: | 1 to 40%, preferably | 2 to 30% |
| Granulates | | |
| active ingredient | 0.5 to 30%, preferably | 3 to 15% |
| solid carrier: | 99.5 to 70%, preferably | 97 to 85% |

The following examples are not intended to limit, but to illustrate the scope of the invention.

A. BIOLOGICAL EXAMPLES

Example 1

Efficacy against Bacteria and Yeasts

Test solutions were prepared by dissolving the compounds shown in Tables 1–4 in 50% ethanol and further diluting with sterile distilled water. These test solutions were pipetted into Petri dishes and mixed with warm tryptose agar to reach an active ingredient concentration of 100 ppm. After cooling, the medium was inoculated with the following yeasts or bacteria:

*Debaryomyces hansenii* (yeast) (A)
*Pseudomonas alcaligenes* (gram neg) (B)
*Bacillus cereus mycoides* (gram pos) (C)
*Pseudomonas aeruginosa* (gram neg) (D)
*Flavobacterium sp.* (gram neg) (E)
*Streptomyces albus* (gram pos) (F)
*Enterobacter aerogenes* (gram neg) (G)
*Escherichia coli* (gram neg) (H)

After sufficient growth of the untreated cultures, the compounds were evaluated using the following rating system:
0=growth equal to control.
1=inhibition of growth by the compound.
2=no growth under the influence of the compound.

The scores measured for antibacterial and antifouling efficacy of the compounds of this invention are listed in Tables 1–4. The sign '—' signifies the compound was not tested.

TABLE 1

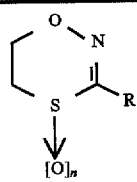

| Compounds | | | Bacteria | | | | | | | |
|---|---|---|---|---|---|---|---|---|---|---|
| Co. no. | n | R | A | B | C | D | E | F | G | H |
| 1 | 1 | 4-chlorophenyl | 2 | 1 | 2 | 0 | 2 | 2 | 0 | 2 |
| 2 | 2 | 2,4-dichlorophenyl | 2 | 0 | 2 | 0 | 2 | 0 | 0 | 0 |
| 3 | 1 | 3-nitrophenyl | 2 | 2 | 2 | 1 | 2 | 2 | 1 | 2 |
| 4 | 1 | 3,4-dichlorophenyl | 2 | 1 | 2 | 0 | 2 | 2 | 0 | 2 |
| 5 | 2 | 2-methylphenyl | 2 | 0 | 0 | 0 | 2 | 2 | 0 | 1 |
| 6 | 1 | 3-fluorophenyl | 2 | 1 | 2 | 0 | 2 | 2 | 0 | 2 |
| 7 | 1 | 2-furanyl | 2 | 1 | 2 | 0 | 2 | 0 | 0 | 0 |
| 8 | 1 | 2-thienyl | 2 | 2 | 2 | 1 | 2 | 2 | 2 | 2 |
| 9 | 1 | 3-methoxyphenyl | 0 | 0 | 0 | 0 | 0 | 0 | 0 | 0 |
| 10 | 1 | 4-methylphenyl | 2 | 1 | 2 | 1 | 2 | 2 | 0 | 2 |
| 11 | 2 | 4-methylphenyl | 2 | 1 | 1 | 1 | 2 | 1 | 0 | 0 |
| 12 | 2 | 2-furanyl | 0 | 0 | 0 | 0 | 0 | 0 | 0 | 0 |
| 13 | 1 | 3-trifluoromethyl phenyl | 2 | 0 | 2 | 0 | 2 | 2 | 0 | 2 |
| 14 | 1 | 4-ethanonephenyl | 2 | 1 | 2 | 1 | 2 | 2 | 0 | 2 |
| 15 | 1 | 2,6-dichlorophenyl | 1 | 0 | 1 | 0 | 0 | 0 | 0 | 0 |
| 16 | 2 | 2,6-dichlorophenyl | 2 | 0 | 2 | 0 | 0 | 0 | 0 | 0 |
| 17 | 2 | phenyl | 0 | 0 | 0 | 0 | 0 | 0 | 0 | 0 |
| 18 | 2 | 4-chlorophenyl | — | 1 | 2 | 0 | 2 | 2 | 0 | 0 |
| 19 | 2 | 3,5-dichlorophenyl | — | 0 | 2 | 0 | 2 | 2 | 0 | 0 |
| 20 | 1 | 4-butoxyphenyl | 0 | 0 | 0 | 0 | 0 | 0 | 0 | 0 |
| 21 | 1 | 3,5-dichlorophenyl | — | 2 | 2 | 0 | 2 | 2 | 0 | 0 |
| 22 | 1 | 4-benzoic acid ethyl ester | — | 1 | 0 | 0 | 2 | 2 | 0 | 0 |
| 23 | 2 | 3-chlorophenyl | 0 | 0 | 0 | 0 | 0 | 0 | 0 | 0 |
| 24 | 2 | 4-trifluoromethyl phenyl | — | 0 | 2 | 0 | 2 | 2 | 2 | 0 |
| 25 | 1 | 4-trifluoromethyl phenyl | — | 1 | 2 | 0 | 2 | 2 | 0 | 0 |
| 26 | 1 | 3-benzoic acid methyl ester | — | 0 | 2 | 0 | 2 | 2 | 0 | 0 |
| 27 | 2 | 3-bromophenyl | — | 1 | 2 | 0 | 2 | 2 | 0 | 2 |
| 28 | 1 | 4-ethoxyphenyl | — | 0 | 0 | 0 | 2 | 2 | 0 | 0 |

TABLE 2

| Co.No. | R¹ | R² | R³ | R⁴ | X | n | M.P.(°C.) |
|---|---|---|---|---|---|---|---|
| 29 | H | H | H | $CO_2CH_3$ | O | 0 | 85–89 |
| 30 | H | H | H | $CO_2CH_3$ | O | 2 | 126–129 |
| 31 | H | H | H | $CO_2CH_3$ | O | 1 | 118–119 |
| 32 | H | $CH_3$ | H | H | S | 0 | oil |
| 33 | H | $CH_3$ | H | H | S | 1 | 73–75 |
| 34 | H | H | H | H | S | 2 | 99–101 |
| 35 | H | H | H | Br | S | 0 | 82–83 |
| 36 | H | H | H | Br | S | 1 | 113–114 |
| 37 | H | $CH_3$ | H | H | S | 2 | 60–62 |
| 38 | H | H | H | Br | S | 2 | 118–119 |
| 39 | H | H | $CO_2CH_3$ | $CH_3$ | O | 0 | 87–88 |
| 40 | H | H | Br | H | S | 0 | 74–75 |
| 41 | H | H | Br | H | S | 1 | 169–173 |
| 42 | H | H | Br | H | S | 2 | 126–127 |
| 43 | H | H | $CO_2CH_3$ | $CH_3$ | O | 2 | 156–157 |
| 44 | H | H | $CO_2CH_3$ | $CH_3$ | O | 1 | 147–148 |
| 45 | H | H | $CH_3$ | $CO_2CH_3$ | S | 1 | 150–152 |
| 46 | H | H | $CH_3$ | $CO_2CH_3$ | S | 2 | 125–126 |
| 47 | H | H | H | $CH_3$ | S | 0 | 62–63 |
| 48 | H | H | H | $CH_3$ | S | 1 | 109–111 |
| 49 | H | H | H | $CH_3$ | S | 2 | 101–102 |
| 50 | $CH_3$ | H | H | H | S | 1 | 114–115 |
| 51 | $CH_3$ | H | H | H | S | 2 | 147–148 |
| 52 | $CH_3$ | H | H | H | S | 0 | 70–72 |
| 53 | H | H | H | $CO_2CH_2CH_3$ | S | 0 | 68–69 |
| 54 | H | H | H | $CO_2CH_2CH_3$ | S | 1 | 109–110 |
| 55 | H | H | H | $CO_2CH_2CH_3$ | S | 2 | 123–124 |
| 56 | H | H | H | CN | S | 0 | 136–137 |
| 57 | H | H | H | CN | S | 1 | 160–162 |
| 58 | H | H | H | CN | S | 2 | 153–155 |
| 59 | H | H | H | Cl | S | 0 | 74–77 |
| 60 | H | H | H | Cl | S | 1 | 102 |
| 61 | H | H | H | Cl | S | 2 | 113–114 |
| 62 | H | H | H | CHO | S | 0 | 48–49 |
| 63 | H | H | H | $NO_2$ | S | 0 | 162–163 |
| 64 | H | H | H | $NO_2$ | S | 1 | 186–188 |
| 65 | H | H | H | $NO_2$ | S | 2 | 160–161 |
| 66 | H | H | H | $CH=NOCH_3$ | S | 2 | 168–170 |
| 67 | H | H | H | $C_6H_5$ | S | 0 | 100–103 |
| 68 | H | H | H | $C_6H_5$ | S | 1 | 144–147 |
| 69 | H | H | H | $C_6H_5$ | S | 2 | 95–98 |
| 70 | H | H | $NO_2$ | $C_6H_5$ | S | 0 | 140–145 |
| 71 | H | H | $CH_3$ | Br | S | 0 | oil |
| 72 | H | H | $CH_3$ | Br | S | 1 | 100–104 |
| 73 | H | H | Br | $CH_3$ | S | 0 | 64–67 |
| 74 | H | H | COOH | $CH_3$ | O | 0 | |
| 75 | H | H | $CONHC_6H_5$ | $CH_3$ | O | 0 | |
| 76 | H | H | $CONHC_6H_5$ | $CH_3$ | O | 0 | |
| 77 | H | H | $CONHC_6H_5$ | $CH_3$ | O | 0 | |

TABLE 2a

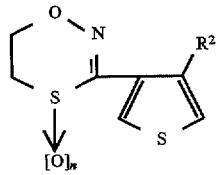

| Co. No. | R² | n | M.P. (°C.) |
|---|---|---|---|
| 78 | H | 2 | 102–104 |
| 79 | H | 1 | 106–107 |

TABLE 3

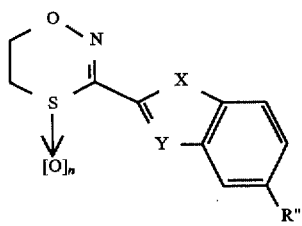

| Co. No. | R" | X | Y | n | M.P.(°C.) |
|---|---|---|---|---|---|
| 80 | H | O | N | 2 | 255 |
| 81 | H | O | N | 1 | 190–191 |
| 82 | H | O | N | 0 | 143–144 |
| 83 | H | S | N | 2 | 226–227 |
| 84 | H | S | N | 0 | 150–151 |
| 85 | H | S | N | 1 | 192–195 |
| 86 | H | S | CH | 0 | 132–134 |
| 87 | H | S | CH | 1 | 140–142 |
| 88 | H | S | CH | 2 | 150–154 |
| 89 | CH₃ | O | N | 1 | 209–210 |
| 90 | CH₃ | O | N | 2 | 215–216 |
| 91 | H | S | C—OCH(CH₃)₂ | 1 | oil |

TABLE 4

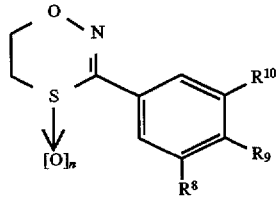

| Co. No. | R⁸ | R⁹ | R¹⁰ | n | M.P.(°C.) |
|---|---|---|---|---|---|
| 92 | H | F | H | 2 | 136–138 |
| 93 | H | F | H | 1 | 132–133 |
| 94 | F | F | H | 2 | 106–108 |
| 95 | F | F | H | 1 | 128–130 |
| 96 | F | F | H | 0 | 63–65 |
| 97 | CF₃ | H | CF₃ | 1 | 110–113 |
| 98 | CF₃ | H | CF₃ | 0 | 44–48 |
| 99 | CF₃ | H | CF₃ | 2 | 76–78 |
| 100 | F | H | F | 0 | 103–104 |
| 101 | F | H | F | 2 | 108–110 |
| 102 | F | H | F | 1 | 138–139 |
| 103 | CO₂CH(CH₃)₂ | Cl | H | 0 | oil |
| 104 | CO₂CH(CH₃)₂ | Cl | H | 1 | 127–129 |
| 105 | CO₂CH(CH₃)₂ | Cl | H | 2 | 82–83 |
| 106 | H | CH=NOCH₃ | H | 1 | 85–87 |
| 107 | H | CH=NOCH₃ | H | 2 | 104–106 |

Example 2

Efficacy against Fresh-water algae 9 ml of Bold's algal broth containing an appropriate concentration of test compound, was inoculated in a 5.5 cm diameter plastic Petri dish with 1 ml of a two week old stock culture of one of three species of green algae (*Chlamydomonas dysosmos, Chlorella vulgaris* or *Ulothrix confervicola*) or the blue-green bacterium *Anabaena cylindrica*. The dishes were incubated in a climate room under a photosynthetically active radiation level of 40 µmole.m⁻²$.sec^{-1}$ at 20° C. during the day (16 h) and 18° C. at night (8 h). Evaluation was performed after 14 days by visually estimating the percentage of algal growth as compared to controls. Results are expressed as minimum test concentration (in ppm) giving 90% mortality.

| Compounds | | | Concentration (ppm) | | | |
|---|---|---|---|---|---|---|
| Co. no. | n | R | Chlamydomonas dysosmos | Chlorella vulgaris | Ulothrix confervicola | Anabaena cylindrica |
| 4 | 1 | 3,4-dichlorophenyl | 2.5 | 10 | 2.5 | 2.5 |
| 8 | 1 | 2-thienyl | 2.5 | 5 | 1 | 2.5 |
| 18 | 2 | 4-chlorophenyl | 2.5 | 10 | 5 | 2.5 |
| 19 | 2 | 3,5-dichlorophenyl | 5 | 10 | 2.5 | 2.5 |
| 21 | 1 | 3,5-dichlorophenyl | 1 | 5 | 1 | 2.5 |
| 25 | 1 | 4-trifluoromethyl phenyl | 2.5 | 10 | 2.5 | 5 |

Example 3

Efficacy against Marine algae 9 ml of Provisoli ASP-2 (Artificial Seawater-2) medium containing an appropriate concentration of test compound, was inoculated in a 5.5 cm diameter plastic Petri dish with 1 ml of a two weeks old stock culture of the diatom *Phaeodactylum tricornutum* or the unicellar red alga *Porphyridium sp*. The dishes were incubated in a climate room under a photosynthetically active radiation level of 40 $\mu mole.m^{-2}.sec^{-1}$ at 20° C. during the day (16 h) and 18° C. at night (8 h). Evaluation was performed after 14 days by visually estimating the percentage of algal growth as compared to controls.

Compounds 1, 2, 3, 4, 5, 14, 15, 16, 18, 19, 21, 25, 27 caused 90% mortality at concentration levels equal to or lower than 1 ppm.

Example 4

Efficacy against Artemia

Into 1 ml of artificial sea-water containing different amounts of the test compound, approximately 15 Artemia Instar II larvae were added. After 24 hours of static incubation with continuous illumination the test was evaluated.

Compounds 2, 4, 5, 11, 13, 18, 19 caused 100% mortality at concentration levels equal to or lower than 10 ppm.

B. COMPOSITION EXAMPLES (ALL PERCENTAGES ARE BY WEIGHT)

Example 5

Composition examples for solid compounds of formula (I)

a) Emulsifiable concentrates: emulsions of any concentration could be obtained from these concentrates by dilution with water.

| | a) | b) |
|---|---|---|
| compound of formula (I) | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| dimethylbenzene mixture | 50% | 79% | b) Dusts: were obtained by mixing the active ingredient with the carriers, and grinding the mixture in a suitable mill.

| | a) | b) |
|---|---|---|
| compound of formula (I) | 0.1% | 1% |
| talcum | 99.9% | — |
| kaolin | — | 99% | c) Suspension concentrates from which suspensions of any desired concentration could be obtained by dilution with water were obtained by intimately mixing finely ground active ingredient with the adjuvants.

| | a) | b) |
|---|---|---|
| compound of formula (I) | 40% | 5% |
| ethylene glycol | 10% | 10% |
| nonylphenol polyethylene glycol ether (15 moles of ethylene oxide) | 6% | 1% |
| sodium lignosulfate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

Example 6

Composition examples for liquid active ingredients of formula (I)

a) Emulsifiable concentrates: emulsions of any concentration could be obtained from these concentrates by dilution with water.

| | a) | b) | c) |
|---|---|---|---|
| compound of formula (I) | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| dimethylbenzene mixture | 70% | 25% | 20% | b) Solutions suitable for application in the form of microdrops.

| | a) | b) | c) | d) |
|---|---|---|---|---|
| compounds of formula (I) | 80% | 10% | 5% | 95% |
| ethylene glycol monoethyl ether | 20% | — | — | — |

-continued

| | a) | b) | c) | d) |
|---|---|---|---|---|
| polyethylene glycol (MG 400) | — | 70% | — | — |
| N-methyl-2-pyrrolidone | — | 20% | — | — |
| epoxidised coconut oil | — | — | 1% | 5% |
| petroleum distillate (boiling range 160–190° C.) | — | — | 94% | — | c) Granulates: prepared by dissolving the active ingredient in dichloromethane, spraying the solution onto the carrier, and subsequently evaporating the solvent.

| | a) | b) |
|---|---|---|
| compound of formula (I) | 5% | 10% |
| kaolin | 94% | — |
| highly dispersed silicic acid | 1% | — |
| attapulgite | — | 90% | d) Dusts: were obtained by intimately mixing the carriers with the active ingredient.

| | a) | b) |
|---|---|---|
| compound of formula (I) | 2% | 5% |
| highly dispersed silicic acid | 1% | 5% |
| talcum | 97% | — |
| kaolin | — | 90% |

Example 7

Composition examples for paints

| a) Compound of formula (I) | 6.0% |
|---|---|
| Titanium dioxide | 17.1% |
| Whiting | 9.7% |
| Talc | 13.2% |
| Calgon | 0.1% |
| Hydroxyethylcellulose (3% solution in water) | 12.5% |
| Co-solvent | 1.2% |
| Minor additives | 0.4% |
| Water | 27.7% |
| Vinyl acetate/versatate copolymer emulsion | 12.1% |
| b) Compound of formula (I) | 1.0% |
| Titanium dioxide | 26.4% |
| Soya alkyd resin | 44.0% |
| White spirit | 27.5% |
| Cobalt octoate (8%) | 0.3% |
| Lead octoate (33%) | 0.7% |
| Methyl ethyl ketoxime | 0.1% |

I claim:

1. A method of controlling bacteria and fouling organisms, said method comprising administering to said bacteria or fouling organisms, or to a non-living material other than wood, an effective antibacterial or antifouling amount of a compound having the formula

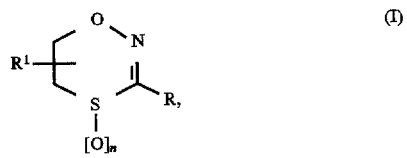

wherein n is 0, 1 or 2; $R^1$ is hydrogen, $C_{1-4}$alkyl or benzyl; and R represents (a) phenyl; phenyl substituted with 1 to 3 substituents independently selected from hydroxyl, halo, $C_{1-12}$alkyl, $C_{5-6}$cycloalkyl, trihalomethyl, phenyl, $C_{1-5}$alkoxy, $C_{1-5}$alkylthio, tetrahydropyranyloxy, phenoxy, $C_{1-4}$alkylcarbonyl, phenylcarbonyl, $C_{1-4}$alkylsulfinyl, $C_{1-4}$alkylsulfonyl, carboxy or its alkali metal salt, $C_{1-4}$alkyloxy-carbonyl, $C_{1-4}$alkylaminocarbonyl, phenylaminocarbonyl, tolylaminocarbonyl, morpholinocarbonyl, amino, nitro, cyano, dioxolanyl or $C_{1-4}$alkyloxyiminomethyl; naphthyl; pyridinyl; thienyl, preferably when n is not 2; furanyl; or thienyl or furanyl substituted with one to three substituents independently selected from $C_{1-4}$alkyl, $C_{1-4}$alkyloxy, $C_{1-4}$alkylthio, halo, cyano, formyl, acetyl, benzoyl, nitro, $C_{1-4}$alkyl-oxycarbonyl, phenyl, phenylaminocarbonyl and $C_{1-4}$alkyloxyiminomethyl; or R represents a radical of formula

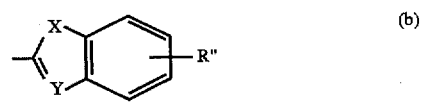

wherein X is oxygen or sulfur; Y is nitrogen, CH or $C(C_{1-4}$alkyloxy); and R" is hydrogen or $C_{1-4}$alkyl.

2. A method according to claim 1 of protecting non-living materials other than wood, and the objects made of or covered by said non-living materials, against bacteria and fouling organisms, said method comprising applying to the surface or incorporating into said materials or objects an effective antibacterial or antifouling amount of a compound of formula (I).

3. A method according to claim 2 wherein the compound of formula (I) is 5,6-dihydro-3-(2-thienyl)-1,4,2-oxathiazine, 4-oxide or 3-(4-chlorophenyl)-5,6-dihydro-1,4,2 -oxathiazine, 4,4-dioxide.

4. A method according claim 2 wherein the non-living material is an adherent coating material such as paint, antifouling paint, varnish, lacquer, finish or whitewash.

5. A method according to claim 4 wherein the adherent coating material is conserved in a storage container or wherein the coating material has been applied as a film to a substrate.

6. A method according to claim 2 for protecting underwater objects whose surfaces are made of materials other than wood, such as shiphulls, harbour installations, drying docks, sluice-gates, locks, mooring masts, buoys, drilling platforms, bridges, pipelines, fishing nets, cables and any other object in constant or frequent contact with water, by applying to said objects an antifouling composition comprising an effective antifouling amount of a compound of formula (I) as defined in claim 1.

7. A method according to claim 2, wherein the mount of the compound of formula (I) ranges from 0.001% to 95% by weight based on the total weight of the composition.

8. A method according to claim 1 wherein the fouling organisms are algae.

9. A method according to claim 1 wherein the fouling organisms are mollusks.

10. A method according to claim 1 wherein the fouling organisms are bacteria.

11. A method according to claim 1 wherein the fouling organisms are crustacea.

* * * * *